United States Patent [19]
Watanabe et al.

[11] 4,273,450
[45] Jun. 16, 1981

[54] PHOTOACOUSTIC SPECTROMETER WITH ANALYSIS-SIGNAL ENHANCEMENT

[75] Inventors: Atsuo Watanabe; Masahiro Uno, both of Kawasaki, Japan

[73] Assignee: Fuji Electric Co., Ltd., Tokyo, Japan

[21] Appl. No.: 80,167

[22] Filed: Sep. 28, 1979

[51] Int. Cl.³ ............................................. G01N 21/00
[52] U.S. Cl. ................... 356/433; 250/345; 324/77 G
[58] Field of Search ............... 356/432, 433; 250/343, 250/345, 346, 461 R; 324/77 G

[56] References Cited

U.S. PATENT DOCUMENTS

| | | | |
|---|---|---|---|
| 3,295,362 | 1/1967 | Wood et al. | 324/77 G |
| 3,631,339 | 12/1971 | Low et al. | 324/77 G |
| 3,700,890 | 10/1972 | Kruezer | 250/343 |
| 3,948,345 | 4/1976 | Rosencwaig | 356/432 |

*Primary Examiner*—Richard A. Rosenberger
*Attorney, Agent, or Firm*—Bruce L. Birchard

[57] ABSTRACT

By autocorrelating the sample photoacoustic response signal and the reference photoacoustic response signal, respectively, obtained from the sample and reference cells, of a photoacoustic spectrometer, and cross-correlating the autocorrelated signals to produce a third signal, simple mathematical operations upon the resulting three signals will produce accurate sample analysis free from the effects of the noise arising from sample illumination intensity variations and other random phenomena.

10 Claims, 4 Drawing Figures

PHOTOACOUSTIC SPECTROMETER WITH ANALYSIS-SIGNAL ENHANCEMENT

BACKGROUND OF THE INVENTION

1. Field of the Invention

This invention relates to photoacoustic spectrometers and, more specifically, to such spectrometers with improved sample analysis capability.

2. Prior Art

Photoacoustic spectrometry has become a popular non-destructive analysis method. It relies upon the fact that various materials, when illuminated, convert the absorbed light into heat at various rates and at various efficiencies. The absorption spectrum is peculiar to each substance. Photoacoustic spectrometry quantifies the heat generation by measuring, directly or indirectly, the thermal expansion of the gas surrounding the sample when the sample is illuminated. One method (and apparatus) for achieving this measurement is shown in co-pending application Ser. No. 55,272 invented by Atsuo Watanabe, et al. and filed July 6, 1979 and assigned to the same assignee as this application. In that apparatus, the rate of flow of gas from an illuminated sample chamber to an un-illuminated reference chamber is measured by means of a flow-meter which produces a periodically interrupted d.c. output corresponding to the pattern of interrupting the illumination to the sample cell. If two such units are utilized and a known material is placed in one sample chamber and an unknown in the other sample chamber, both chambers being illuminated by chopped light from a common monochromatic light source, a relatively accurate analysis of the composition of the unknown sample is possible. However, time variations in light intensity and chopping frequency produce spurious phenomena or "noise" in the test results and inaccuracy in the related analysis. One factor of great importance in achieving accuracy of analysis is the time delay in the sample-response signal relative to the illuminating signal.

Prior art devices did not have accurate means for determining such delay—referred to as "$\theta$," a phase-angle. Also, as the frequency of light chopping is varied as part of the analysis technique, phase is not necessarily preserved and the accuracy of "$\theta$" is adversely affected.

Many conventional photoacoustic spectrometers can produce both in-phase and quadrature outputs, but such dual-phase-output spectrometers are no more accurate than single-phase-output spectrometers as far as "$\theta$" is concerned. In such dual-phase-output spectrometers the "in-phase" output signal is produced by synchronous rectification in a phase condition where the signal is at is maximum. The quadrature output is produced by a 90° phase delay. Producing an accurate 90° phase shift at these low chopping frequencies is very difficult and analysis inaccuracies result.

Therefore, it is an object of the present invention to overcome the general disadvantages set forth hereinbefore.

It is a further object of the present invention to provide a photoacoustic spectrometer with enhanced sample analysis capabilities.

It is a still further object of this invention to provide a photoacoustic spectrometer which is free of synchronous rectification requirements.

SUMMARY OF THE INVENTION

Stated succinctly, in a photoacoustic spectrometer, by autocorrelating the electrical signal from the unknown-sample unit, autocorrelating the electrical signal from the reference-sample unit and cross-correlating the resulting signals to produce a third signal, by straight forward mathematical operations such as division, square-root extraction and multiplication, the three signals may be used to provide accurate characteristics of the unknown sample, such as the time-lag angle "$\theta$."

BRIEF DESCRIPTION OF THE DRAWINGS

The present invention, both as to its nature and scope, may best be understood by reference to the description, herein, taken in connection with the drawings, in which.

DETAILED DESCRIPTION OF THE PREFERRED EMBODIMENTS

Figures 1, 2:
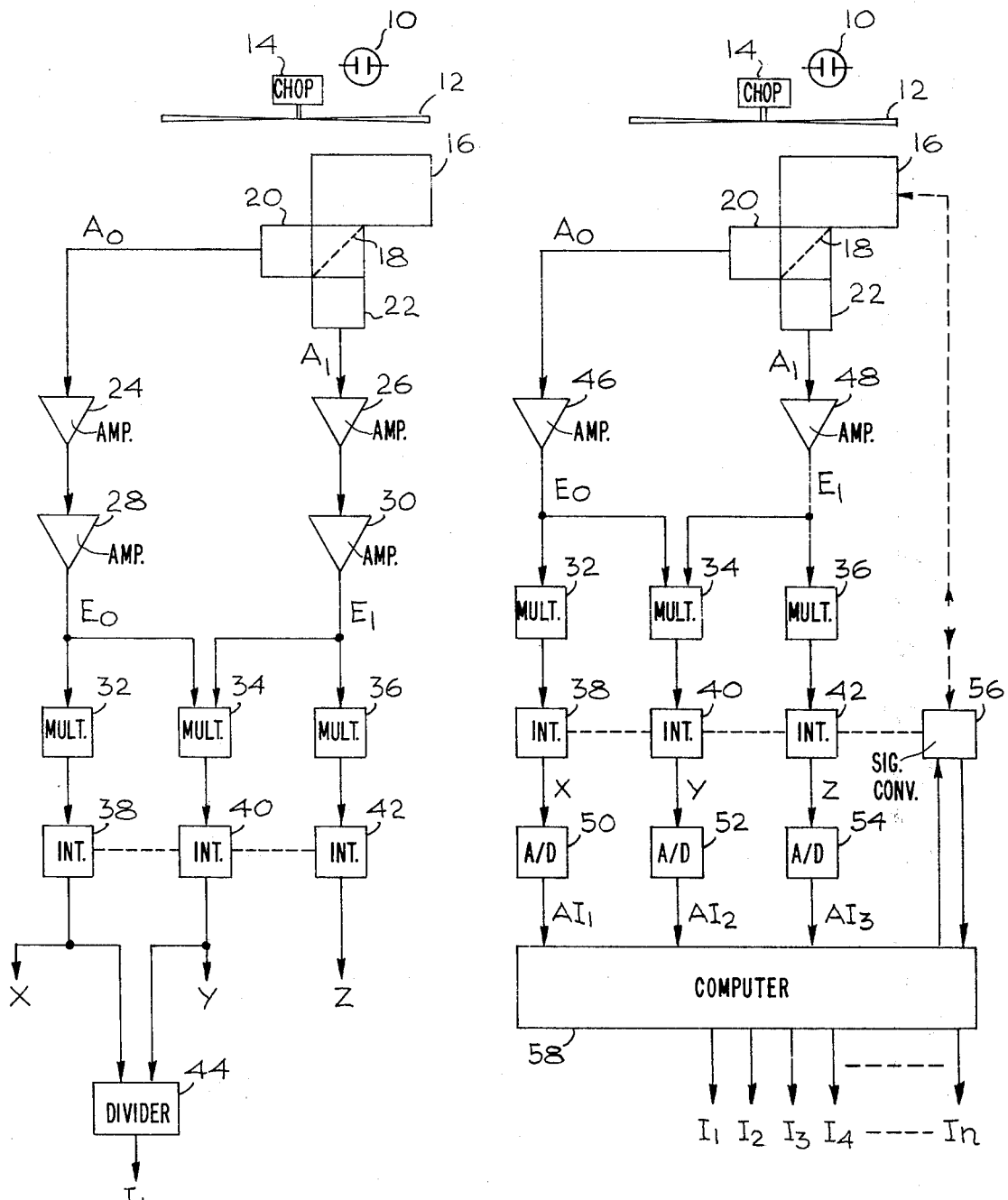
FIG. 1 is a block diagram showing one embodiment of this invention.
FIG. 2 is a block diagram showing a second embodiment of this invention.

In FIG. 1, light source 10 may be a xenon lamp. Chopper 12 is driven by its motor 14, which may be capable of speed variation. Light from lamp 10 passes (when chopper 12 permits it to do so) into monochromator 16.

Such monochromators being available commercially need no description here. The output light from monochromator 16 passes into beam-splitter 18, which may contain a half-silvered mirror. There the beam is split, half passing into reference cell 20 which contains a reference material and the other half passing into sample cell 22 which contains a sample to be analyzed. Output signal ($A_0$) from cell 20 passes to pre-amplifier 24. Output signal ($A_1$) from sample cell 22 passes to pre-amplifier 26. After pre-amplification, signal $A_0$ passes to tuned main amplifier 28. Signal $A_1$, after pre-amplification, passes to tuned main amplifier 30. Amplifiers 28 and 30 are sharply tuned to the frequency of chopper 12. As a result, signals $E_0$ and $E_1$ are of the same frequency as the light chopping frequency. Tuning adjustments of amplifiers 28 and 30 can be done manually, as is more evident in FIG. 3. Amplification of amplifiers 24, 26, 28 and 30 can be adjusted manually, as is evident from the circuit of FIG. 3. To perform the step, identical samples of material (such as carbon black) are placed in cells 20 and 22 and the gain of each of the amplifying channels is adjusted until $E_0 = E_1$.

The reference and sample signals $E_0$ and $E_1$, are of periodic waveform, the dominant component of which has the frequency of chopper 12. The two signals may be defined as:

$$E_0 = A_{E0} \sin wt;$$

and, $$E_1 + A_{E1} \sin (wt - \theta);$$

where A is the amplitude of the respective signal, w is $2\pi$ times the chopping frequency and $\theta$ is the phase difference in the signals produced by the absorptionradiation characteristics of the unknown and sample reference materials.

Continuing with FIG. 1, reference signal $E_0$ is multiplied by itself (squared) in multiplier 32. Signals $E_0$ and $E_1$ are multiplied by each other in multiplier 34. Signal $E_1$ is squared in multiplier 36. Integrators 38, 40 and 42 simultaneously integrate the output signals from multipliers 32, 34 and 36, respectively, over predetermined and equal, time periods. The predetermined time period for integration should be equal to an integer multiple of the period of signals $E_0$ and $E_1$, i.e., an integer multiple of the reciprocal of the light chopping frequency. Information on the time period corresponding to the light-chopping frequency can be derived from chopper 12 by optical or magnetic means and supplied to integrators 38, 40 and 42.

The output signals from integrators 38 and 42 represent the autocorrelation functions (X and Z) (i.e., the durationally-averaged self-multiplications) of signals $E_0$ and $E_1$, respectively. The output signal from integrator 40 (Y) represents the cross-correlation function (i.e., the durationally averaged product) of the reference signal $E_0$ and the sample signal $E_1$, respectively.

The reference character "X" may be defined as follows:

$$X \alpha \overline{A_{E0}^2 \sin^2 wt} = \overline{A_{E0}^2(1-\cos^2 wt)} \alpha A_{E0}^2,$$

where the overlying bar indicates averaging with respect to time for a certain duration equal to an integer multiple of a cycle period of the function-more particularly, the integral with respect to time for that duration divided by that duration. As indicated, X is proportional to the square of the luminous flux density from source 10.

The output of integrator 42, representing the autocorrelations function of the sample signal $E_1$, has been denoted by the reference character Z, which can be expressed as:

$$Z \alpha \overline{A_{E1}^2 \sin^2(wt-\theta)} \alpha A_{E1}^2,$$

indicating that Z is also proportional to the luminous flux intensity from source 10.

The output of integrator 40, representing the cross-correlation function of the reference signal $E_0$ and the sample signal $E_1$ is designated by the reference character "Y." "Y" may be defined as follows:

$$Y \alpha \overline{A_{E0}A_{E1} \sin wt \sin(wt-\theta)}$$
$$= \overline{A_{E0}A_{E1}(\sin^2 wt \cos\theta - \sin wt \cos wt \sin\theta)}$$
$$= A_{E0}A_{E1}\cos\theta$$

Since $\overline{\sin wt \cos wt}$ equals zero. The output signals X and Y are fed to divider 44 to produce an output signal, $I_1$, which is equal to Y/X. This $I_1$, represents the photoacoustic output signal corresponding to the sample being analyzed corrected with respect to the luminous flux intensity of the light source.

Thus, the signal processing circuit of this invention produces the value of the photoacoustic output $I_1$ of the examined sample and the values of its associated correlation and autocorrelation functions X, Y and Z. As occasion demands, those values can be supplied to square-root extractors, dividers and/or multipliers, to produce data for qualitative determination of the sample in real-time processing.

For example, the time lag $\theta$ of the sample's photoacoustic signal with respect to the reference signal is given by $$\frac{Y}{\sqrt{XZ}} = \cos\theta.$$

The amplitudes $A_{E0}$ and $A_{E1}$ of the reference and sample signals $E_0$ and $E_1$ can be given by $\sqrt{X}$ and $\sqrt{Z}$, so that, if photoacoustic measurement takes place while varying the frequency of incident light, a difference in spectrum between photoacoustic responses of the reference material and the sample can be given by $\sqrt{X} - \sqrt{Y}$. As the value of $\sin\theta$ can be obtained from the above $\cos\theta$, a quadrature output of the photoacoustic spectrometer can be also obtained by the operation of $Y/X \tan\theta$. Other operations can give additional data for qualitative study.

Those operations can be carried out in either an analog or a digital computer.

An embodiment of the invention combined with a digital computer for the foregoing purpose is shown in FIG. 2. Here, the circuit from the light source 10 to the integrators 38, 40 and 42 is similar to that shown in FIG. 1, but the pre-amplifier 24 and the main amplifier 26 with its resonant circuit, are combined as a tuned amplifier 46, and similarly, the preamplifier 26 and the main amplifier 30 are shown as another tuned amplifier 48. Reference numerals 50, 52 and 54 designate analog/digital converters. 56 is another signal converter section having a digital/analog converting capability (which will be discussed in more detail later, herein), and 58 is a computer.

The outputs X, Y and Z are led through respective analog/digital converters 50, 52 and 54 to the computer 58, the latter performingg various mathematical operations to produce outputs $I_1, I_2, \ldots, I_n$, among which are, for example: output $I_1$ representing the photoacoustic output of the examined sample corrected with respect to the luminous flux intensity of the light source, and given by:

$$I_1 = Y/X;$$

output $I_2$ serving to indicate the phase difference between the sample signal and the reference signal, and given by:

$$I_2 \ Y/\sqrt{XZ} = \cos\theta;$$

and outputs $I_3$ and $I_4$ representing the amplitudes $A_{E0}$ and $A_{E1}$ of the reference and sample signals $E_0$ and $E_1$ respectively, and given by $$I_3 = \sqrt{X}$$
$$I_4 = \sqrt{Z} \ ;$$

so that, if the photoacoustic measurement takes place while varying the frequency of the incident light, a computation of $I_3 - I_4$ will give the difference in photoacoustic output spectrum between the examined sample and the reference material. Because $I_2 = \cos\theta$ is given, another output $I_5 = \sin \theta$ can be obtained, and a quadrature output signal lagging by 90° behind the sample signal can be also calculated by the computer, 58.

If an output $I_6$ representing the durationally averaged product of the sample signal $E_1$ and a quadrature reference signal lagging by 90° the signal $E_0$ and subjected to correction for the intensity of the light source, is required, it can be calculated in the computer 58 by solving the equation:

$$I_6 = \frac{A_1}{A_0} \cdot \overline{\cos wt - \sin(wt - \theta)} = \frac{A_1}{A_0} \sin\theta$$

$$= \sqrt{\frac{X}{Z}} \cdot \sin\theta$$

Further an output $I_7$ representing the ratio between the amplitudes of the reference and sample signals can be found by solving the equation:

$$I_7 = \sqrt{\frac{X}{Z}}.$$

The mathematical operations performed in computer 58 take a finite time. Consequently it is preferable to adjust or determine the duration of integration in the integrators 38, 40 and 42, the scanning speed in the monochromator 16 and timings of signals to and from the computer 58, so as to make them compatible with the speed of the computer 58. To this end, in the embodiment shown in FIG. 2, the computer 58 supplies control signals through a signal converter section 56 (including digital/analog converting means) to the integrators 38, 40 and 42 and to the monochromator 16. The signal converter section 56 is also provided with analog/digital converting means to supply reference information to the computer 58, e.g., the light chopping frequency from the monochromator 16.

As mentioned earlier herein, in the signal processing circuits of this invention, the reference and sample signals, extracted by the tuned amplifiers (such as amplifiers 46 and 48) from the photoacoustic cell outputs, are supplied to respective series combinations of a multiplier and an integrator, which produce the durationally averaged self-multiplications (autocorrelation signals) and products of the reference and sample signals (cross-correlation signals) or equivalents of them, and then such outputs are supplied through analog/digital conversion to computing means 58 to give the final outputs required. Thus the invention, with neither synchronous rectification nor reference-signal phase shifting, produces a photoacoustic spectrometry result inclusive of measurement of the phase difference of the reference signal and the sample signal and corrected with respect to the luminous flux intensity of the light source 10.

Figure 3A:
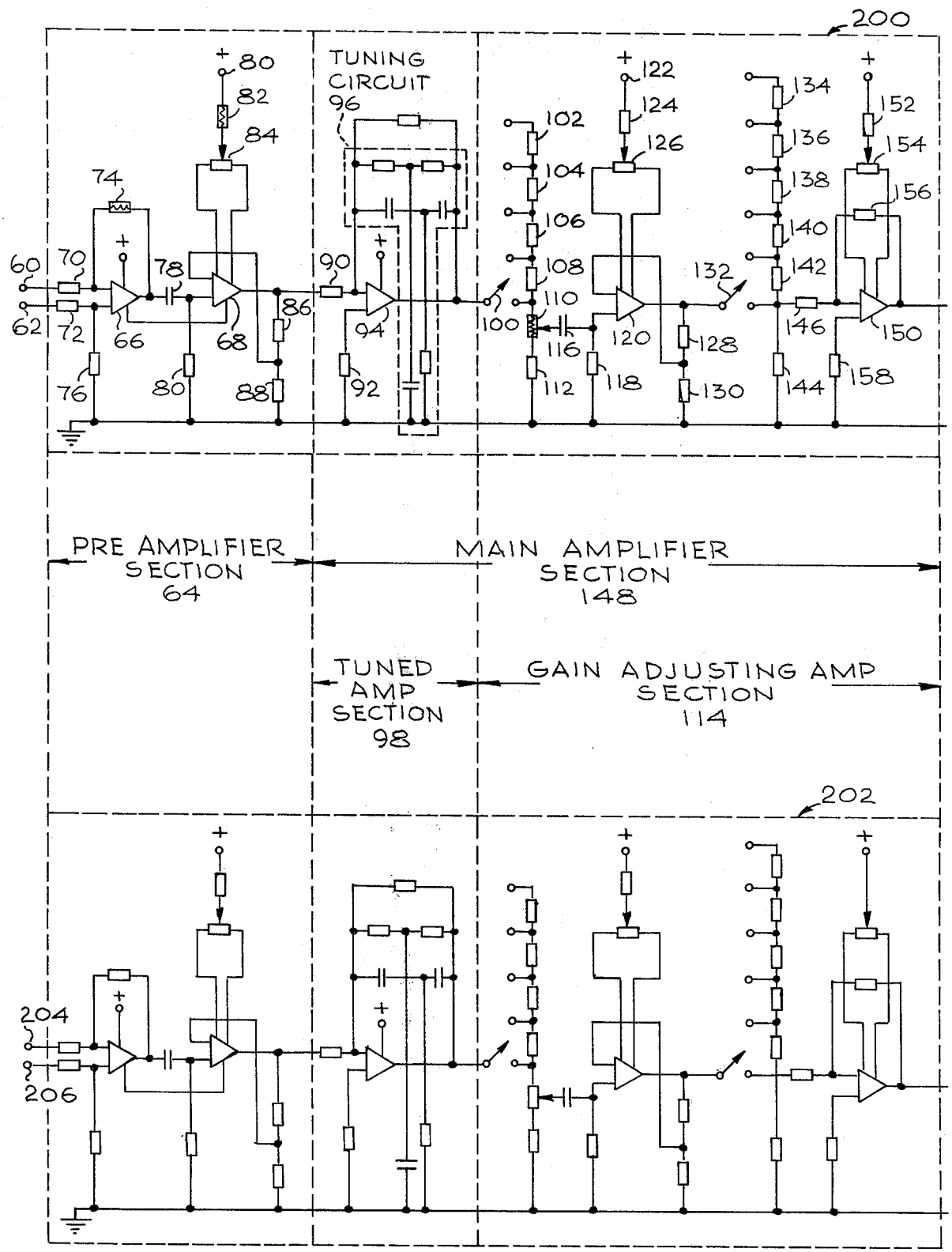
FIGS. 3A, 3B is a circuit diagram of one form of the embodiment of FIG. 1.
Figure 3B:
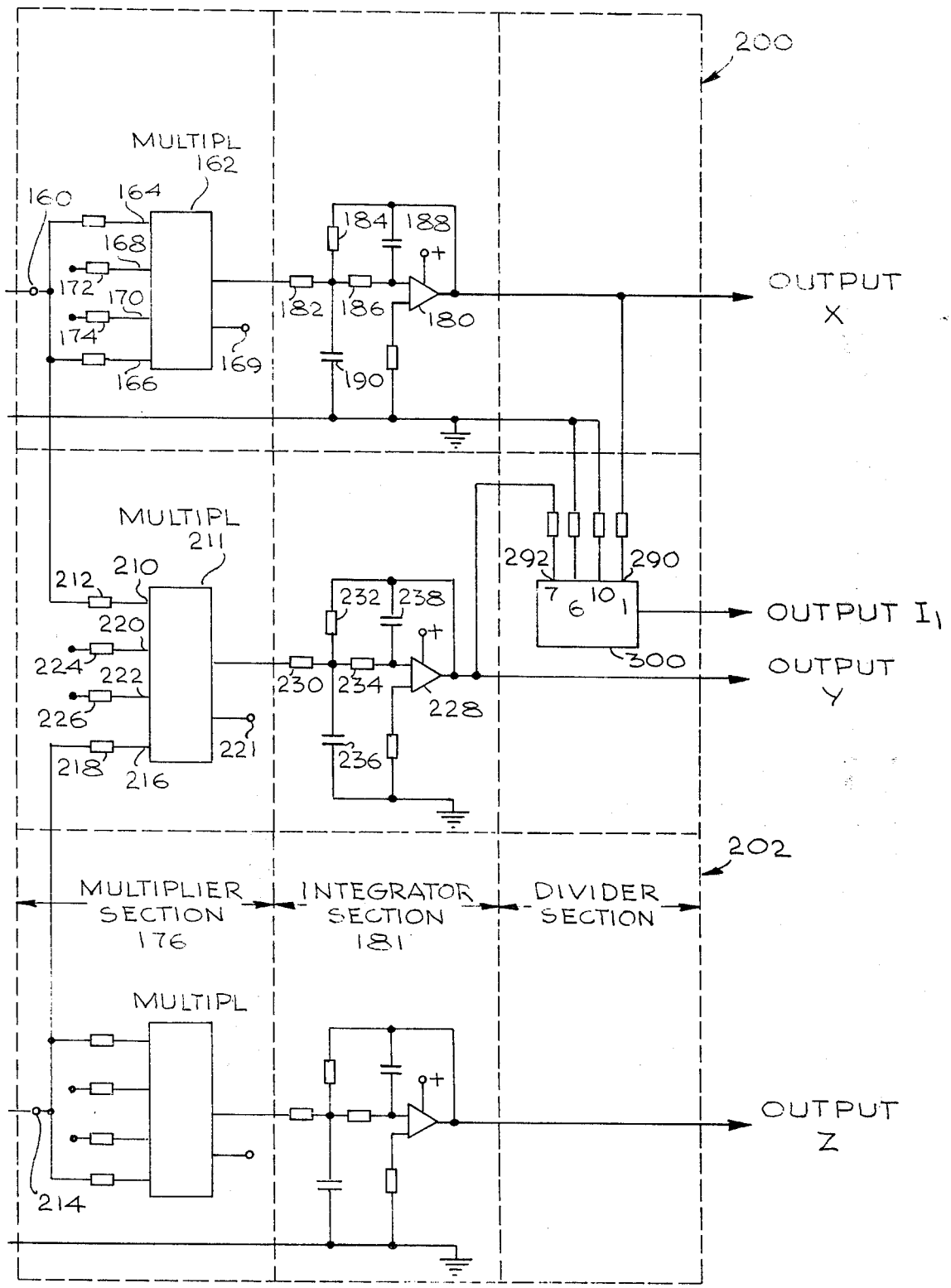

One form of a more detailed circuit diagram for the configuration of FIG. 1 is set forth in FIG. 3. In FIG. 3, chopped d.c. signals of either polarity from the flowmeter element in associated photoacoustic reference coil 20 is introduced, alternatively, at input terminals 60 and 62 for pre-amplification by the variable-gain pre-amplifier comprising amplifier chips 66 and 68. Chip 66 may be a type OP-O5CT available from Precision Monolithics, Inc. of the United States. Chip 68 may be, for example, a type μPC159 available from Nippon Electric Co., Ltd. of Japan. Resistors 70 and 72, in combination with resistors 74 and 76 permit coupling the desired level of reference signal from cell 20 (FIG. 1) to amplifier chip 66. Similarly, condenser 78 and resistor 80 couple the signal from chip 66 to chip 68 in pre-amplifier 64. Proper operating voltage for chip 68 is provided from a positive terminal 80 to chip 68 through resistor 82 and potentiometer 84. Resistors 86, 88, 90 and 92 perform normal signal forward and feedback coupling and biasing functions. Chip 94, in combination with the R-C tuning network 96 constitutes a tuned amplifier 98 the response of which is peaked at the chopping frequency to pass a narrow band of frequencies around the chopping frequency.

The output of tuned amplifier 98 is coupled through stepping switch 100 and its associated voltage divider, comprising resistors 102 through 112, to gain adjusting amplifier 114; through the coupling network comprising condenser 116 and resistor 118 to chip 120, the operating potential for which is obtained from positive source terminal 122 through resistor 124 and potentiometer 126. Appropriate feedback is provided by resistors 128 and 130. The output of chip 120 is coupled through step switch 132 and its associated voltage divider network comprising resistors 134 through 144, and through coupling resistor 146 to the final stage of amplification in main amplifier 148, comprising chip 150 and its associated biasing and coupling resistors 152 through 158.

Chips 68, 94, 120 and 150 may be of the type μPC159 available from Nippon Electric Co., Ltd. of Japan.

The output signal from the reference signal channel of main amplifier 148 appears at terminal 160 and from there it is provided to multiplier chip 162 in multiplier section 176 through inputs 164 and 166. Offset adjusting potentials are applied to terminals 168, 169 and 170 of multiplier chip 162 through resistors 172 and 174. Multiplier chip 162 may be a type AD543L available from Analog Devices Inc. of the U.S. The self-multiplied-reference-signal output from multiplier chip 162 is then coupled to integrator chip 180, in integrator section 181 through coupling resistor 182 and and R-C integrating network including resistors 184 and 186 and condensers 188 and 190. The output "X" is an autocorrelated reference signal.

Sample signal channel 202 is identical to the reference signal channel 200 except that the input signal at input terminal 204 or 206 is derived from sample cell 22 instead of from sample cell 20 and the output signal from channel 202 is the signal Z, an autocorrelation of the input sample signal instead of the input reference signal.

The selectively amplified reference signal, before self-multiplication, is taken from terminal 160 and fed to one input terminal 210 of multiplier chip 211 through coupling resistor 212. Similarly, the selectively amplified sample signal, before self-multiplication, is fed from terminal 214 in channel 202 to input terminal 216 of multiplier chip 211 through resistor 218.

Offset-adjusting voltages are applied to terminals 220, 221 and 222 of multiplier 211 through resistors 224 and 226, respectively. Multiplier 211 may be a type AD524L chip available from Analog Devices, Inc. of the U.S.A.

The cross-multiplied output signal from multiplier 211 is fed to integrator chip 228 through resistor 230. An integrating network comprising resistors 232 and 234 and condensers 236 and 238 is coupled to chip 228, as shown. Chip 228, as well as chip 180, may be a type μA741 available from Fairchild Camera and Instrument Corporation of the U.S.A.

The output signal "Y" from chip 228 is a cross-correlation signal of the reference and sample signals.

Signal X and Signal Y are fed to terminals 290 and 292 of divider chip 300, which may be a type AD534L from Analog Devices, Inc. In divider chip 300 the quotient Y/X (which represents the photoacoustic output signal derived from the sample, corrected for any variations in the intensity of light from source 10) is obtained and is designated $I_1$, in this discussion. Appropriate operating voltages are provided for the various chips from a conventional power supply not shown.

By placing identical materials, say lampblack, in both the reference and sample cells and adjusting the gain in channels 200 and 202, the system may be set up to eliminate any inherent differences in the channels so that only actual differences between he sample and the reference will influence the determination of the qualitative characteristics of the sample in cell 22.

While particular embodiments have been shown and described it is apparent to those skilled in the art that variations or modifications may be made without departing from the spirit and scope of this invention. It is the purpose of the appended claims to cover all such modifications and variations.

What is claimed is:

1. The method of accurately determining the physical characteristics of a sample material by photoacoustic spectrometry which includes the steps of;
   producing an electrical reference-signal representative of the light-to-heat conversion characteristics of a known reference material;
   producing an electrical sample-signal representative of the light-to-heat conversion characteristics of a sample material having physical characteristics under study;
   producing a reference autocorrelation signal corresponding to said electrical reference-signal;
   producing a sample autocorrelation signal corresponding to said electrical sample-signal;
   cross-correlating said reference autocorrelation signal and said sample autocorrelation signal to produce a cross-correlation signal; and
   performing predetermined mathematical operations upon selective combinations of said reference autocorrelation signal, said sample autocorrelation signal and said cross-correlation signal to derive desired physical characteristics of said sample material.

2. The method according to claim 1 in which the mathematical operations include dividing the cross-correlation signal by the square-root of the product of the reference autocorrelation signal and the sample correlation signal to give the phase difference between the sample signal and the reference signal.

3. Apparatus for photoacoustic spectrometry including;
   reference means for producing a reference electrical signal representative of the light-to-heat conversion characteristics of a known reference material;
   sample means for producing a sample electrical signal representative of the light-to-heat conversion characteristics of a sample material having physical characteristics under study;
   first autocorrelation means coupled to said reference means and responsive to the reference electrical signal therefrom to produce a first autocorrelation signal;
   second autocorrelation means coupled to said sample means and responsive to the sample electrical signal therefrom to produce a second autocorrelation signal;
   cross-correlation means coupled to said first and second autocorrelation signals, respectively, to produce a cross-correlation signal; and,
   computing means coupled to said cross-correlation means, to said first autocorrelation means and to said second autocorrelation means and responsive to the respective signals therefrom to calculate selected characteristics of said sample material.

4. Apparatus according to claim 3 in which said first and second autocorrelating means each includes multiplying means, and integrating means coupled to said multiplying means.

5. Apparatus according to claim 3 in which said computing means includes a divider coupled to said first autocorrelation means and to said cross-correlation means and responsive to the respective signals therefrom to produce a signal representative of the photoacoustic response of said sample corrected for any variations in the level of illumination of said sample.

6. Apparatus according to claim 3 which includes, in addition, analog-to-digital converting means coupled between said first and second autocorrelation means and said cross-correlation means, on the one hand, and said computing means, on the other hand.

7. Apparatus according to claim 3 in which said reference means and said sample means each includes a tuned amplifier.

8. Apparatus according to claim 3 in which said reference means and said sample means each includes an adjustable-gain amplifier.

9. Apparatus according to claim 3 in which said reference means and said sample means each includes a pre-amplifier with dual-polarity-input-signal capability.

10. Apparatus according to claim 3 in which said reference means and said sample means both include a source of chopped light of a pre-determined chopping frequency and each such means includes an amplifier tuned to said chopping frequency.

* * * * *